US009347806B2

(12) United States Patent  
Kim et al.

(10) Patent No.: US 9,347,806 B2  
(45) Date of Patent: May 24, 2016

(54) SENSOR HAVING AN EMBEDDED ELECTRODE, AND METHOD FOR MANUFACTURING SAME

(71) Applicants: JOINSET CO., LTD., Ansan-si, Kyeonggi-do (KR); EXPANTECH CO., LTD., Hwaseong-si, Gyeonggi-do (KR)

(72) Inventors: Sun-Ki Kim, Gunpo-si (KR); Sung-Youl Kim, Seongnam-si (KR); Hyun-Hak Jung, Ansan-si (KR); Jung-Suk Kim, Hwaseong-si (KR)

(73) Assignees: Joinset Co., Ltd. (KR); Expantech Co., Ltd. (KR)

( * ) Notice: Subject to any disclaimer, the term of this patent is extended or adjusted under 35 U.S.C. 154(b) by 177 days.

(21) Appl. No.: 14/034,859

(22) Filed: Sep. 24, 2013

(65) Prior Publication Data

US 2014/0041464 A1 Feb. 13, 2014

Related U.S. Application Data

(63) Continuation of application No. PCT/KR2012/002153, filed on Mar. 23, 2012.

(30) Foreign Application Priority Data

Mar. 24, 2011 (KR) .......................... 10-2011-0026380  
Mar. 15, 2012 (KR) .......................... 10-2012-0026553

(51) Int. Cl.
*G01D 21/00* (2006.01)  
*G01N 27/30* (2006.01)

(52) U.S. Cl.
CPC ................ *G01D 21/00* (2013.01); *G01N 27/30* (2013.01); *Y10T 29/49208* (2015.01)

(58) Field of Classification Search
None  
See application file for complete search history.

(56) References Cited

U.S. PATENT DOCUMENTS 6,202,471 B1 * 3/2001 Yadav et al. ................. 73/31.05  
8,402,813 B2 * 3/2013 Kruse et al. .................. 73/23.33  
2004/0177685 A1 * 9/2004 Yokura et al. .............. 73/335.04

FOREIGN PATENT DOCUMENTS

| JP | 8-261979 A | 10/1996 |
| JP | 2002-148343 A | 5/2002 |
| KR | 10-0355688 B1 | 9/2002 |
| KR | 10-2006-0110278 A | 10/2006 |
| KR | 10-2010-0111558 A | 10/2010 |

\* cited by examiner

*Primary Examiner* — Robert R Raevis  
(74) *Attorney, Agent, or Firm* — Park & Associates IP Law, P.C.

(57) ABSTRACT

Disclosed is a sensor having an embedded electrode, which can be manufactured at a reduced cost and applied to many different fields. The sensor comprises: a sensing stack in which a first conductive layer and a second conductive layer are stacked and layered with a separation layer interposed therebetween; and an electrode terminal arranged at a side surface of the sensing stack and electrically connected to the first and second conductive layers. The first and second conductive layers are exposed on at least one side surface of the sensing stack except for the side surface on which the electrode terminal is arranged, to thereby form a sensing surface.

12 Claims, 7 Drawing Sheets

SENSOR HAVING AN EMBEDDED ELECTRODE, AND METHOD FOR MANUFACTURING SAME

REFERENCE TO RELATED APPLICATIONS

This is a continuation of pending International Patent Application PCT/KR2012/002153 filed on Mar. 23, 2012, which designates the United States and claims priority of Korean Patent Application No. 10-2011-0026380 filed on Mar. 24, 2011 and Korean Patent Application No. 10-2012-0026553 filed on Mar. 15, 2012, the entire contents of which are incorporated herein by reference.

FIELD OF THE INVENTION

The present invention relates to a sensor having an embedded electrode, and a method for manufacturing the same, and more particularly, to a sensor having an embedded electrode, which is capable of being manufactured at a reduced cost and applied to various fields, and a method for manufacturing the same.

BACKGROUND OF THE INVENTION

In general, a structure of a sensor for sensing bio-gas or infrared optical materials and a method for manufacturing the same have been developed.

In most sensors, a pair of sensing electrode patterns is formed on a substrate, and a sensing membrane that is coated with a sensing material is formed on the pair of sensing electrode patterns.

In these sensors, when gas or light contacts the sensing membrane, the sensing membrane may be changed in conductivity (or resistance). Thus, the sensor may sense the gas or light by measuring the change in conductivity.

Most of these sensors are manufactured by using a semiconductor process such as a thin film formation process using a silicon substrate or manufactured by using a thick film formation process using an aluminum substrate. As a result, their manufacturing costs may be expensive, and also, their manufacturing process may be complicated. In addition, defects due to the short-circuit or disconnection of the sensing electrode or defects due to the delamination of the sensing electrode may occur.

SUMMARY OF THE INVENTION

Accordingly, an object of the present invention provides a sensor having an embedded electrode.

Another object of the present invention provides a sensor having an embedded electrode, which is capable of being manufactured at a reduced cost.

Further another object of the present invention provides a sensor having an embedded electrode, of which a manufacturing process is simplified.

Further another object of the present invention provides a sensor having an embedded electrode, in which a fine pattern is capable of being formed with less costs.

Further another object of the present invention provides a sensor having an embedded electrode, by which accurate sensing is enabled.

Further another object of the present invention provides a sensor having an embedded electrode, which has improved reliability.

Further another object of the present invention provides a sensor having an embedded electrode, in which a sensing electrode is freely adjusted in length, width, and size.

Another object of the present invention provides a method for manufacturing the above-described sensor.

According to an aspect of the present invention, there is provided a sensor having an embedded electrode, the sensor including: a sensing stack in which first and second conductive layers are stacked and embedded within a material, the material including a separation layer between the conductive layers; and first and second electrode terminals electrically connected to the first and second conductive layers, the electrode terminal being disposed on a side surface of the sensing stack, wherein the first and second conductive layers are exposed to at least one side surface except for the side surfaces on which the electrode terminals are disposed to form a sensing surface.

At least one slot or groove may be formed in the sensing surface over an overall region in the stacked direction.

The side surface on which the electrode terminal is disposed and the sensing surface may be vertically cut or polished to provide a flat plane.

The first and second conductive layers may overlap each other, or embedded ends of the first and second conductive layers may be spaced apart from each other and do not overlap each other.

The first and second conductive layers may have lengths different from each other so that portions of the first and second conductive layers overlap each other, and remaining portions do not overlap each other.

The electrode terminal may be electrically separated and divided into a plurality of sub electrode terminals for each conductive layer to constitute a plurality of independent sensor modules, and the conductive layers having different numbers may be electrically connected to the plurality of sub electrode terminals, respectively.

The electrode terminal may extend to an opposite side surface of the sensing surface, and each of the first and second conductive layers may be electrically connected to the electrode terminal at the extending portion of the electrode terminal.

According to another aspect of the present invention, there is provided a method for manufacturing a sensor having an embedded electrode, the method including: stacking first and second conductive layers with a separation layer therebetween to form a sensing stack; forming a first electrode terminal to which the first conductive layer exposed to one side surface of the sensing stack is electrically connected and a second electrode terminal to which the second conductive layer exposed to the other side surface of the sensing stack is electrically connected; and exposing the first and second conductive layers to at least one side surface of remaining side surfaces except for the one side surface and the other side surface of the sensing stack to form a sensing surface and apply a sensing material on the sensing surface, thereby forming the sensor.

The one side surface and the other side surface of the sensing stack may be vertically cut or polished.

The first and second conductive layers may be stacked to overlap each other, or embedded ends of the first and second conductive layers may be spaced apart from each other and do not overlap each other.

The first and second conductive layers may have lengths different from each other and be stacked on each other so that portions of the first and second conductive layers overlap each other, and remaining portions do not overlap each other.

The method may further include forming a slot in the sensing surface over an overall region in the stacked direction.

A groove or slot may be formed in the sensing surface to expose all of the first and second conductive layers.

The method may further include plating sectional surfaces of the exposed first and second conductive layers to grow a metal and applying the sensing material between ends of the first and second conductive layers, on which the metal is grown, to planarize the sectional surfaces of the first and second conductive layers.

According to further another aspect of the present invention, there is provided a sensor having an embedded electrode, the sensor including: a sensing stack in which first and second conductive layers are embedded; and an electrode terminal electrically connected to the first and second conductive layers, the electrode terminal being disposed on a side surface of the sensing stack, wherein the first and second conductive layers are exposed to at least one side surface except for the side surface on which the electrode terminal is disposed to form a sensing surface.

According to further another aspect of the present invention, there is provided a sensor having an embedded electrode, the sensor including: a sensing stack in which first and second conductive layers are stacked and embedded with a separation layer therebetween; and an electrode terminal electrically connected to the first and second conductive layers, the electrode terminal being disposed on a side surface of the sensing stack, wherein at least one groove or slot having a predetermined width is formed in at least one side surface except for the side surface on which the electrode terminal is disposed to form a sensing surface, and the first and second conductive layers are exposed to a bottom of the groove or slot or to a bottom and sidewall of the groove or slot.

According to the above-described structure, the conductive layers may be easily adjusted in width and length, and the separation layer may be easily adjusted in thickness. Thus, the sensing electrodes constituted by the conductive layers and the electrode terminals may be easily adjusted in width and length and in distance therebetween.

Also, since the conductive layers constituting the sensing electrodes are embedded into the sensing stack, the short-circuit or disconnection of the electrode may not occur to improve reliability and sensibility of the sensor.

Also, since the slot is formed in the sensing surface, the sensing surface may easily accurately increase or decrease.

Also, since the conductive layers are easily adjusted in number, the sensor may be adjusted in sensibility. That is, the sensibility of the sensor may be improved by using the one sensing stack without connecting a plurality of sensors to each other in parallel or series as described in the related art.

Also, since the ceramic process is applied, the manufacturing process may be simplified, and the manufacturing costs may be reduced.

Furthermore, the sensor according to the present invention may be variously applicable to the sensor for sensing the bio-gas or infrared optical materials. Also, the sensor may be used an antenna by mounting the electrode terminals on a circuit board and using the sensing surface as a receiving surface for receiving signals. Also, the sensor may be used as an arrestor for discharging by using one electrode terminal as a ground terminal and using the conductive layers which are insulated from each other by the insulating separation layer.

DETAILED DESCRIPTION OF THE INVENTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

First Embodiment

Figure 1:
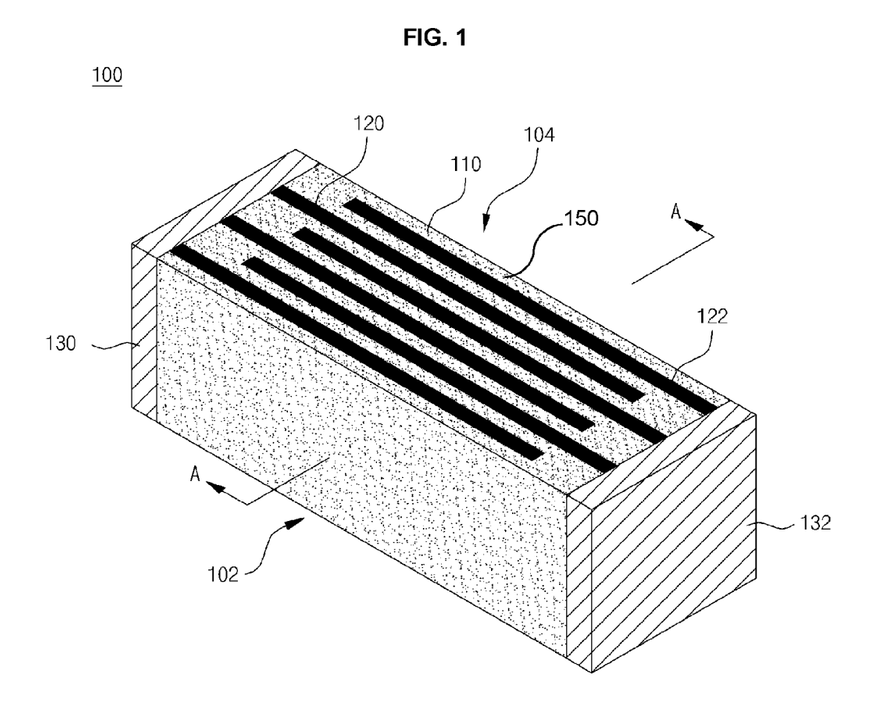
FIG. 1 is a perspective view of a sensor according to a first embodiment of the present invention.

FIG. 1 is a view of a sensor 100 according to a first embodiment of the present invention.

The sensor 100 includes a sensing stack 102 in which conductive layers 120 and 122 are stacked and embedded with a separation layer 110 therebetween and electrode terminals 130 and 120 respectively electrically connected to the conductive layers 120 and 122 and are disposed on side surfaces of the sensing stack 102. The conductive layers 120 and 122 may be exposed to at least one side surface of the sensing stack 102 except for the side surfaces on which the electrode terminals 130 and 132 are disposed, thereby defining a sensing surface 104.

The conductive layer 120 is exposed to only one side surface of the sensing stack 102 and electrically connected to the electrode terminal 130 to constitute one sensing electrode of the sensor 100, and the conductive layer 122 is exposed to only an opposite side surface of the sensing stack 102 and electrically connected to the electrode terminal 132 to constitute the other sensing electrode.

According to the above-described structure, the conductive layers 120 and 122 may be easily adjusted in width and length, and the separation layer 110 may be easily adjusted in thickness. Thus, the sensing electrodes constituted by the conductive layers 120 and 122 and the electrode terminals 130 and 132 may be easily adjusted in width and length and in distance therebetween.

Also, since a ceramic process is applied, the manufacturing process may be simplified, and the manufacturing cost may be reduced.

Also, since the conductive layers 120 and 122 constituting the sensing electrodes are embedded into the sensing stack 102, short-circuit or disconnection of the electrode may not occur to improve reliability and sensibility of the sensor 100.

Also, since the conductive layers 120 and 122 are easily adjusted in number, the sensor 100 may be adjusted in sensibility. That is, the sensibility of the sensor 100 may be improved by using the one sensing stack 102 without connecting a plurality of sensors to each other in parallel or series as described in the related art.

The sensor 100 according to the present invention may be variously applied as a sensor for sensing bio-gas or infrared optical materials.

Also, the sensor 100 may be used an antenna by mounting the electrode terminals 130 and 132 on a circuit board and using the sensing surface 104 as a receiving surface for receiving signals. Particularly, the separation layer 110 may be adjusted in magnetic permeability to control receiving sensitivity.

Also, the sensor 100 may be used as an arrestor for discharging by using one electrode terminal as a ground terminal and using the conductive layers 120 and 122 which are insulated from each other by the insulating separation layer 110.

Figure 2:
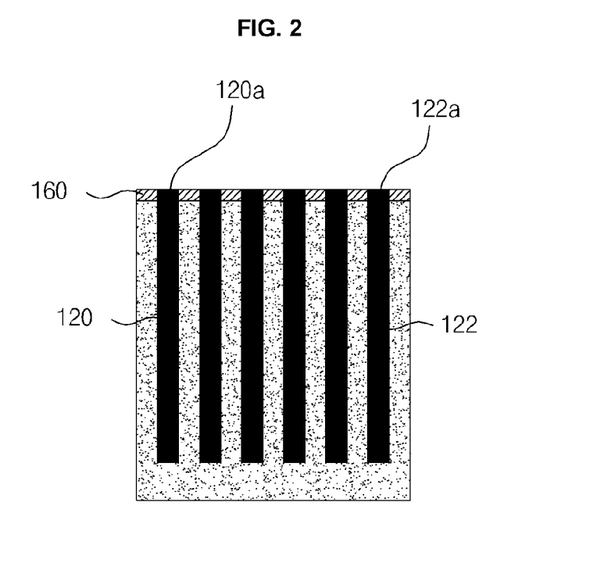
FIG. 2 is a cross-sectional view taken along line A-A of FIG. 1 and illustrates an example in which a sensing material is applied to a sensing surface.

FIG. 2 is a cross-sectional view taken along line A-A of FIG. 1 and illustrates an example in which a sensing material is applied to a sensing surface, thus, forming a sensing material layer on the sensing surface.

Various kinds of sensing materials 150 corresponding to materials to be sensed may be applied to the sensing surface 104 to operate as a sensor. If necessary, a heater (a heating pattern) may be further provided to constitute the sensor 100.

As shown in FIG. 1, the separation layer 110 and the conductive layers 120 and 122 may be disposed to have the same height, and a sensing material may be applied to the separation layer 110 and the conductive layers 120 and 122. If necessary, the conductive layers 120 and 120 may be disposed at heights greater than that of the separation layer 110.

For example, when the sensor 100 is used as a hydrogen sensing sensor, a hydrogen sensing material, e.g., a platinum catalyst, may be applied to the sensing surface 104. However, in this case, there is a limitation that it is difficult to bond platinum to the ceramic for forming the sensing stack 102.

Referring to FIG. 2, a zinc oxide layer 160 that is easily bonded to platinum may be disposed first to apply the platinum that is the hydrogen sensing material. Then, the platinum may be applied on the zinc oxide layer 160. In this case, since the conductive layers 120 and 122 have to be exposed to the outside, it may be necessary to form the conductive layers 120 and 122 to a thickness greater than that of the zinc oxide layer 160.

For this, sections of the conductive layers 120 and 122 may be plated to grow a metal, thereby increasing a height of an end of each of the conductive layers 120 and 122. Then, the zinc oxide layer 160 may be formed on an entire surface to planarize the zinc oxide layer 160 by a polishing process, thereby applying the platinum catalyst to the zinc oxide layer 160.

The above-described structure is not limited to the platinum sensing material. That is, when a sensing material that is difficult to be bonded to the sensing stack 102 is applied, the platinum sensing material may be applicable.

Also, the separation layer 110 may be etched so that the conductive layers 120 and 122 have relatively higher heights in addition to the method in which the sections of the conductive layers 120 and 122 are plated to grow the metal, thereby increasing the heights of the conductive layers 120 and 122.

Hereinafter, a method for manufacturing the sensor 100 according to an embodiment will be described.

Figure 3:
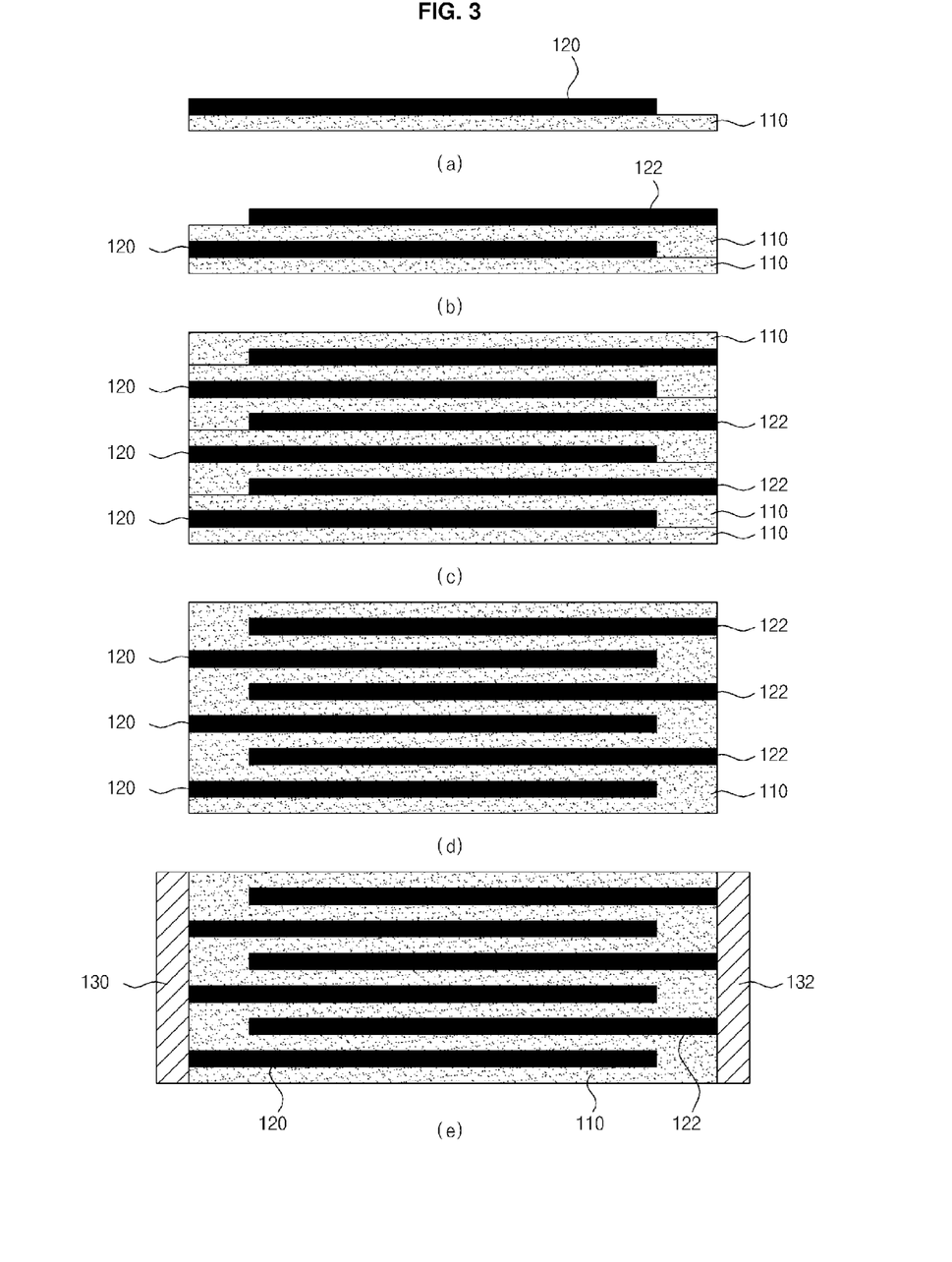
FIGS. 3(a) to 3(e) are sequentially arranged sectional views illustrating a method for manufacturing a sensor according to an embodiment.
Figure 4:
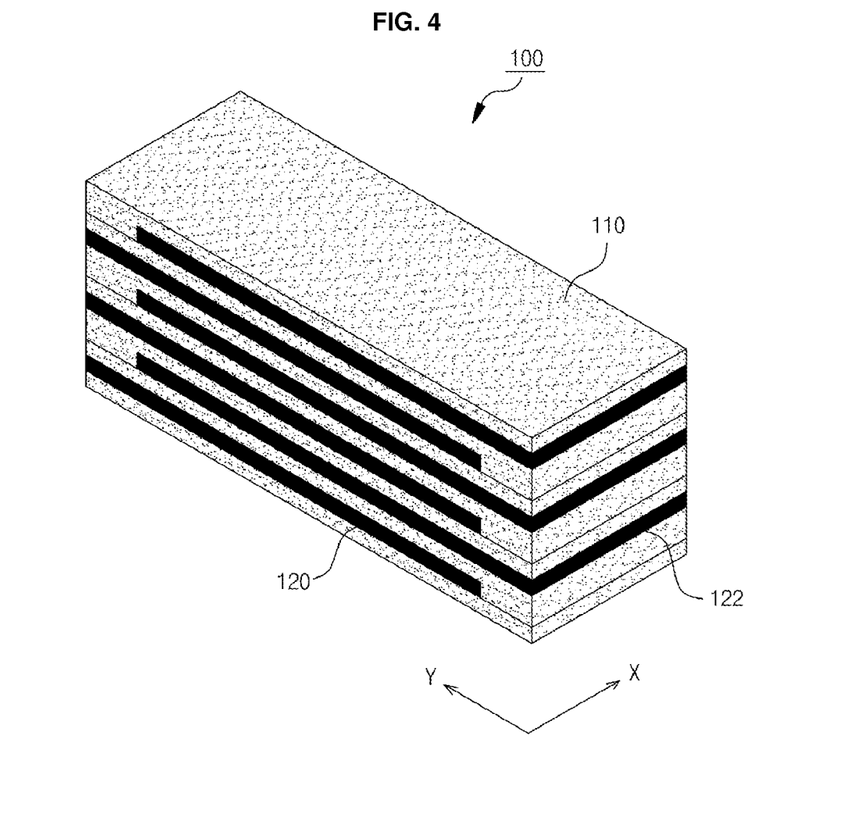
FIG. 4 is a perspective view of a manufactured sensing stack.

FIG. 3 is a view illustrating a method for manufacturing the sensor 100 according to an embodiment, and FIG. 4 is a view of the manufactured sensing stack 102.

Referring to FIG. 3A, a separation layer 110 is formed. The separation layer 110 may be formed of various materials such as insulating materials such ceramic or resin, piezoelectric materials, and semiconductor materials according to a function or sensing object of the sensor 100.

Next, a conductive layer 120 is formed on the separation layer 110. The conductive layer 120 is exposed to one side surface (for example, a left surface in FIG. 3) and is not exposed to an opposite side surface (for example, a right surface).

Here, the conductive layer 120 may not be exposed or may be exposed to other side surfaces except for the one side surface and the opposite side surface. That is, at least one side surface of other side surfaces except for the one side surface and the opposite side surface may be used as the sensing surface 104. Here, even though the conductive layer 120 is not exposed to the side surface to be used as the sensing surface 104, the sensing surface 104 may be formed by performing a cutting, polishing, or groove formation process as a post-process.

The conductive layer 120 may be formed of any material that contains platinum, silver, gold, or an alloy thereof to realize superior conductivity. The conductive layers 120 and 122 may be formed of the same material or formed of materials different from each other. For example, the conductive layer 120 may be formed of a nickel material, and the conductive layer 122 may be formed of a platinum material.

Referring to FIG. 3B, the separation layer 110 and the conductive layer 122 are additionally stacked on the structure including the conductive layer 120. Since the separation layer 110 formed on the conductive layer 120 is formed of the same material as the separation layer 110 formed in FIG. 3A, the separation layers 110 are denoted by like reference numeral and name.

The conductive layer 122 may have the same material or formation method as the conductive layer 120 except that the conductive layer 122 is exposed to the opposite side surface and is not exposed to the one side surface. Similarly, the conductive layer 122 may not be exposed or may be exposed to other side surfaces except for the one side surface and the opposite side surface.

Hereinafter, for convenience of description, the side surfaces to which the conductive layers 120 and 122 are exposed, i.e., the one side surface and the opposite side surface are referred to as "electrode terminal installation surfaces".

Referring to FIG. 3C, the processes described with reference to FIGS. 3A and 3B may be repeatedly performed to repeatedly arrange a structure stacked in an order of the separation layer 110, the conductive layer 120, the separation layer 110, and the conductive layer 122, thereby forming a sensing stack 102. If necessary, the separation layer 110 may be interposed to adjust the number of stacked conductive layers 120 and 122.

The uppermost portion of the sensing stack 102 is covered by the separation layer 110. FIG. 4 is a perspective view of the sensing stack 102 manufactured as described above.

Referring to FIG. 4, the sensing stack 102 has a structure in which the separation layer 110 is interposed to alternately stack and arrange the conductive layers 120 and 122, and the uppermost and lowermost portions are covered by the separation layer 110.

All conductive layers 120 are exposed to only one side surface of the sensing stack 102, and all conductive layer 122 are exposed to only an opposite side surface of the sensing stack 102. Then, electrode terminals 130 and 132 to be connected to the outside in a post-process are disposed on the one side surface and the opposite side surface.

In a case where the separation layers 110 are formed of the same material in the sensing stack 102 having the above-described structure, as shown in FIG. 3B, the conductive layers 120 and 122 may be embedded and stacked within one separation layer 110, or the conductive layers 120 and 122 may be embedded and stacked within the sensing stack 102. In the above-described structure, the number of conductive layers 120 and 122 embedded and stacked within the sensing stack 102 may increase by increasing the number of stacked structure or the stacked number.

Thereafter, if necessary, a cutting process for vertically cutting the sensing stack 102 or a polishing process for polishing the sensing stack 102 may be performed to process the side surfaces of the sensing stack 102. Here, the cutting process or the polishing process may be performed only when necessary.

For example, when it is intended to form the electrode terminals 130 and 132 on the electrode terminal installation surfaces, since the conductive layers 120 and 122 protruding from the electrode terminal installation surfaces are different in protruding degree, it may be necessary to perform the cutting or polishing process so as to planarize the electrode terminal installation surfaces. Similarly, since the conductive layers 120 and 122 protruding from the side surface selected as the sensing surface 104 are different in protruding degree, it may be necessary to planarize the side surface.

If the cutting or polishing process is performed, byproducts generated by the cutting or polishing process may remain on the cut or polished surface. Thus, an etching, cleaning, or thermal treating process may be performed on the cut or polished surface to remove the byproducts. When the etching or cleaning process is performed, the exposed conductive layers 120 and 122 may be recessed into the separation layer 110. On the other hand, when the thermal treating process is performed, the exposed conductive layers 120 and 122 may slightly protrude from the separation layer 110.

Referring to FIG. 4, if the sensing stack has a rectangular shape, both side surfaces facing each other in a Y-axis direction may be used as the electrode terminal installation surfaces, and both side surfaces facing each other in an X-axis direction may be used as the sensing surface 104. Alternatively, only one of both side surfaces may be used as the sensing surface 104.

Although at least one of the two side surfaces except for the electrode terminal installation surfaces is used as the sensing surface in FIG. 4, a cut surface that is newly formed by vertically cutting the sensing stack 102 may be used as the sensing surface in addition to the side surfaces. As a result, if the sensing stack 102 is vertically cut along the X-axis and thus is divided into a plurality of sensing stacks in FIG. 4, a plurality of sensors using the cut surfaces as the sensing surface may be manufactured.

As shown in FIG. 3E, the electrode terminals 130 and 132 are disposed on the electrode terminal installation surfaces of the sensing stack 102, respectively. Each of the electrode terminals 130 and 132 may function as a terminal to be connected to the outside. Also, all conductive layers are electrically connected to the electrode terminal 130, and all conductive layers 122 are electrically connected to the electrode terminal 132.

Although the cutting and polishing processes for forming the sensing surface are performed before the electrode terminals 130 and 132 are formed in the above-described embodiment, the present invention is not limited thereto. For example, the cutting and polishing processes may be performed after the electrode terminals 130 and 132 are formed. Alternatively, as shown in FIG. 4, the plurality of sensors each having the sensing surface may be manufactured.

Second Embodiment

Figure 5:
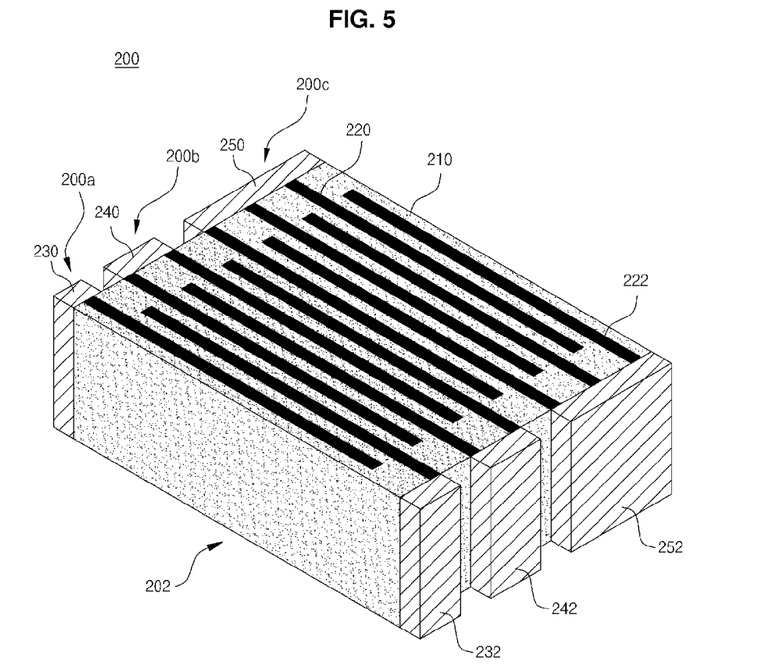
FIG. 5 is a perspective view of a sensor according to another embodiment of the present invention.

FIG. 5 is a view of a sensor 200 according to another embodiment of the present invention.

A plurality of conductive layers 220 and 222 are embedded within one sensing stack 202 in a state where the conductive layers 220 and 222 are separated from each other by a separation layer 210. Also, a plurality of sub electrode terminals 230, 240, 250, 232, 242, and 252 are disposed on electrode terminal installation surfaces to constitute independent sensors 200a, 200b, and 200c.

The sub electrode terminals 230, 240, and 250 disposed on one side surface and the sub electrode terminals 232, 242, and 252 disposed on an opposite side surface are electrically separated from each other. In this embodiment, the conductive layers 220 and 222 having numbers different from each other are connected to each other. For example, one conductive layer may be connected to each of the sub electrode terminals 230 and 232, and two conductive layers may be connected to each of the sub electrode terminals 240 and 242. Also, three conductive layers may be connected to each of the sub electrode terminals 250 and 252.

Alternatively, the conductive layers having the same number may be connected to each of the sub electrode terminals 230, 232, 240, 242, 250, and 252.

Due to the above-described structure, the three sensors 200a, 200b, and 200c which are substantially independent from each other are formed on one sensing stack 202. Here, different sensing materials may be applied to the sensing surface of each of the sensors to sense a plurality of materials at a specific place. Alternatively, if the same sensing material is applied to the sensing surfaces, one material may be sensed.

In this embodiment, one sensing stack 202 may function as the plurality of sensors 200a, 200b, and 200c while the one sensing stack 202 is maintained as it is, unlike the sensing stack 102 of FIG. 4, which is cut and divided into the plurality of sensing stacks 102 to constitute the plurality of sensors.

Third Embodiment

Figure 6:
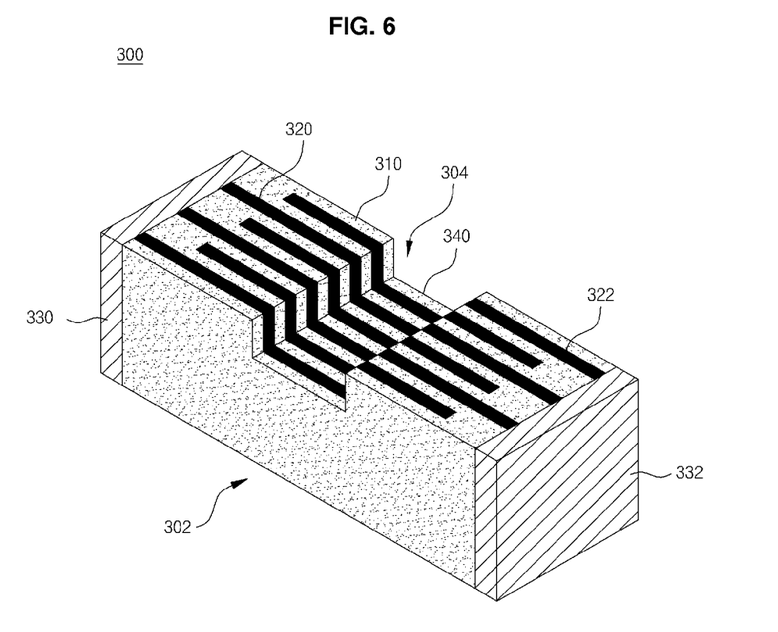
FIG. 6 is a perspective view of a sensor according to further another embodiment of the present invention.

FIG. 6 is a view of a sensor 300 according to further another embodiment of the present invention.

A plurality of conductive layers 320 and 322 are alternately arranged and embedded within one sensing stack 302 with a separation layer 310 therebetween. The conductive layer 320 has an end exposed to only one side surface and thus is electrically connected to an electrode terminal 330 disposed on the side surface. The conductive layer 322 has an end exposed to only an opposite side surface and thus is electrically connected to an electrode terminal 332 disposed on the opposite side surface.

An edge of one side of each of the plurality of conductive layers 320 and 322 is exposed to one side surface of the sensing stack 302 except for the side surface on which the electrode terminals 330 and 332 are disposed to form a sensing surface 304. A slot 340 is formed in the sensing surface 304 over an overall region in a stacked direction of the conductive layers 320 and 322.

Although one slot 340 is formed in this embodiment, a plurality of slots 340 may be formed parallel to each other. The slot 340 may vary in sectional shape, number, size, or depth as necessary. That is, the slot 340 may have various shapes and structures.

According to the above-described structure, each of the conductive layers 320 and 322 exposed to the sensing surface 304 may be freely adjusted in length. As a result, a sensing electrode may be adjusted in length, and the sensing surface 304 may be freely adjusted in size. The length of the sensing electrode and the size of the sensing surface 304 may be adjusted by controlling, for example, a width or depth of the slot 340.

The slot 340 may have an uneven inner surface. A sensing material to be applied to the sensing surface 304 may be applied with a predetermined thickness along the inner surface of the slot 340 or applied to fill the slot 340 so that an entire surface of the sensing surface 304 is planarized.

Forth Embodiment

Figure 7A:
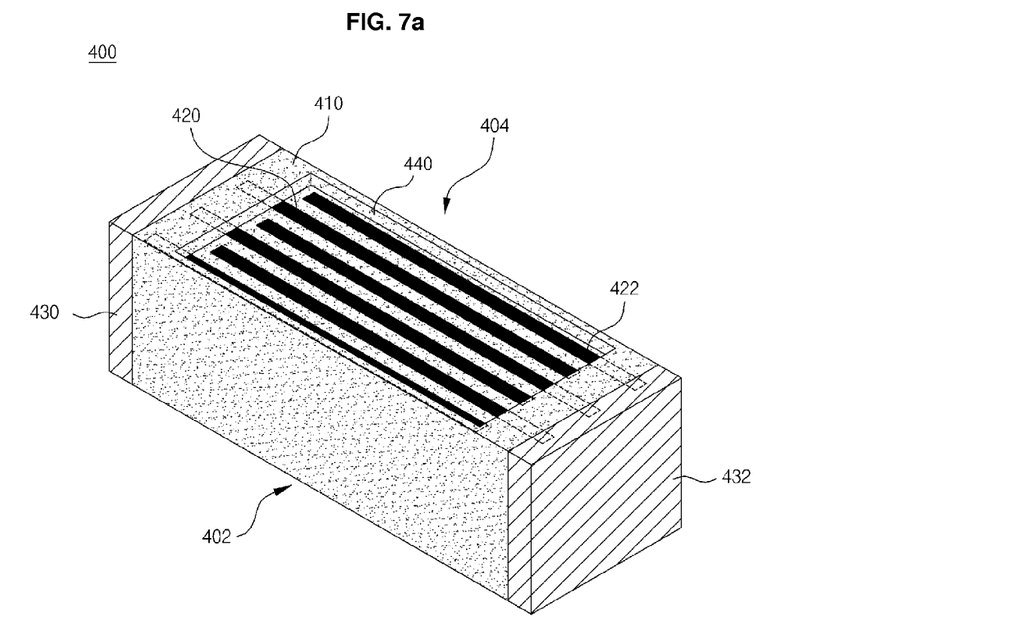
FIGS. 7a and 7b are respectively perspective views of a sensor according to further another embodiment of the present invention.
Figure 7B:
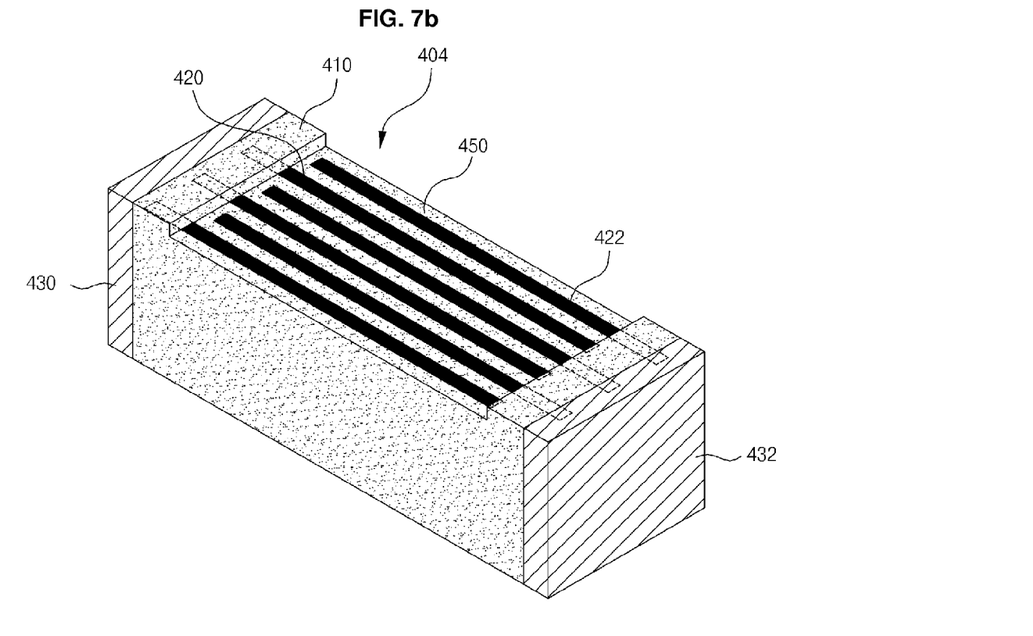

FIGS. 7a and 7b each show a view of a sensor 400 according to further another embodiment of the present invention.

A plurality of conductive layers 420 and 422 are alternately arranged and embedded within one sensing stack 402 with a separation layer 410 therebetween. The conductive layer 420 has an end exposed to only one side surface and thus is electrically connected to an electrode terminal 430 disposed on the side surface. The conductive layer 422 has an end exposed to only an opposite side surface and thus is electrically connected to an electrode terminal 432 disposed on the opposite side surface.

A groove 440 is formed in one side surface except for the side surfaces on which the electrode terminals 430 and 432 are disposed to expose an edge of one side of each of the electrode terminals 430 and 432 to a bottom of the groove 440, thereby forming a sensing surface 404. That is to say, the sensing surface 404 is formed through a window defined by the groove 440.

When the groove 440 has a depth greater than that at which the electrode terminal 430 and 432 are initially exposed, an inner surface of the groove 440 may be used as the sensing surface 404 to increase a size of the sensing surface 404.

Although one groove 440 is formed in this embodiment, a plurality of grooves 440 may be formed parallel to each other. The groove 440 may vary in number or size as necessary. That is, the groove may have various shape and structures. For example, the groove 440 may be determined in size so that the ends of the conductive layers 420 and 422 embedded within the sensing stack 402 are exposed or not. Also, the groove 440 may be adjusted in depth to expose the conductive layers 420 and 422 to the bottom and sidewall of the groove 440 (see FIG. 9).

Also, a sensing material to be applied to the sensing surface 404 may be applied with a predetermined thickness on the bottom of the groove 440 or applied to fill the groove 440. The groove may have an uneven inner surface, but have not a flat inner surface. As, as shown in FIG. 7B, a groove 450 having both edges opened in a stacked direction may be formed. In this case, the groove 450 may be easily formed when compared to that of FIG. 7A.

According to this embodiment, the grooves 440 and 450 may be adjusted in number and width or depth to adjust the size of the sensing surface 404.

In the embodiment described with reference to FIGS. 6 and 7, after the slot 340 and the grooves 440 and 450 are formed, if necessary, an etching, cleaning, or thermal treating process may be performed to clear up the sensing surfaces 304 and 404.

Fifth Embodiment

Figure 8A:
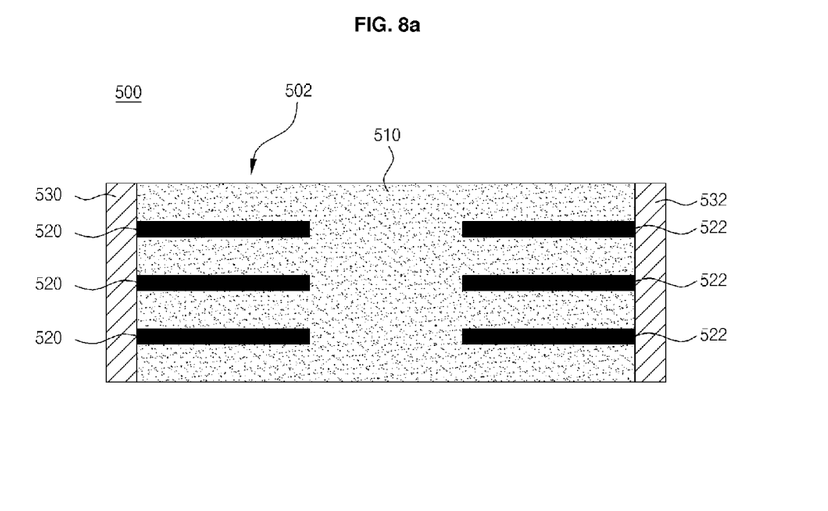
FIGS. 8a and 8b are respectively sectional views of a sensor according to further another embodiment of the present invention.
Figure 8B:
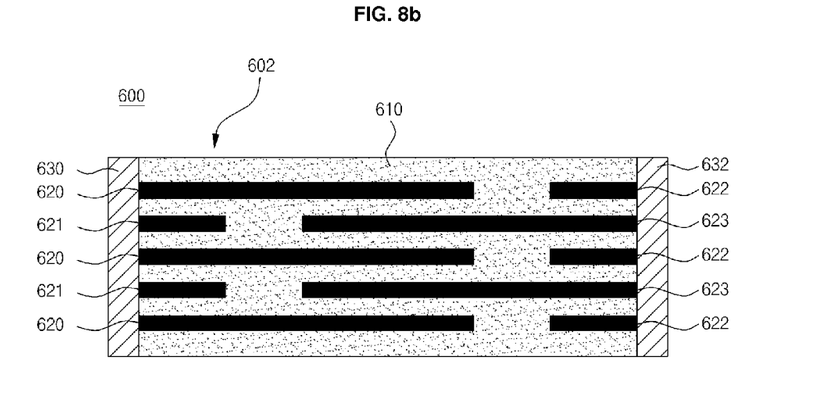

FIGS. 8a and 8b each show a view of sensors 500 and 600 according to further another embodiment of the present invention.

Referring to FIG. 8A, a conductive layer 520 electrically connected to an electrode terminal 530 and a conductive layer 522 electrically connected to an electrode terminal 532, which are embedded within a sensing stack 502, do not overlap each other within the sensing stack 502.

Also, as shown in FIG. 8B, conductive layers embedded within a sensing stack 602 and electrically connected to electrode terminals 630 and 632 may have lengths different from each other so that the conductive layers overlap each other or do not overlap each other within the sensing stack 502. Referring to FIG. 8B, each of the conductive layers 620 and 623 has a length greater than that of each of the conductive layers 621 and 622 to overlap each other. Here, the conductive layers 621 and 622 each having a relatively short length may not overlap each other.

As described above, if only one end of each of the conductive layers is exposed and electrically connected to the electrode terminal, and an edge of at least one side of each of the conductive layers is exposed to satisfy conditions for forming a sensing surface, the conductive layers may have any configuration structure or arrangement structure. In addition, various arrangement structures including an arrangement structure that is well-known to a person skilled in the art may be enabled.

Although the conductive layers are exposed to only side surfaces opposite to each other to allow the electrode terminals to face each other in this embodiment, the conductive layers may vary in pattern to allow the electrode terminals to be respectively disposed on sides adjacent to each other or on the same side surface.

Figure 9:
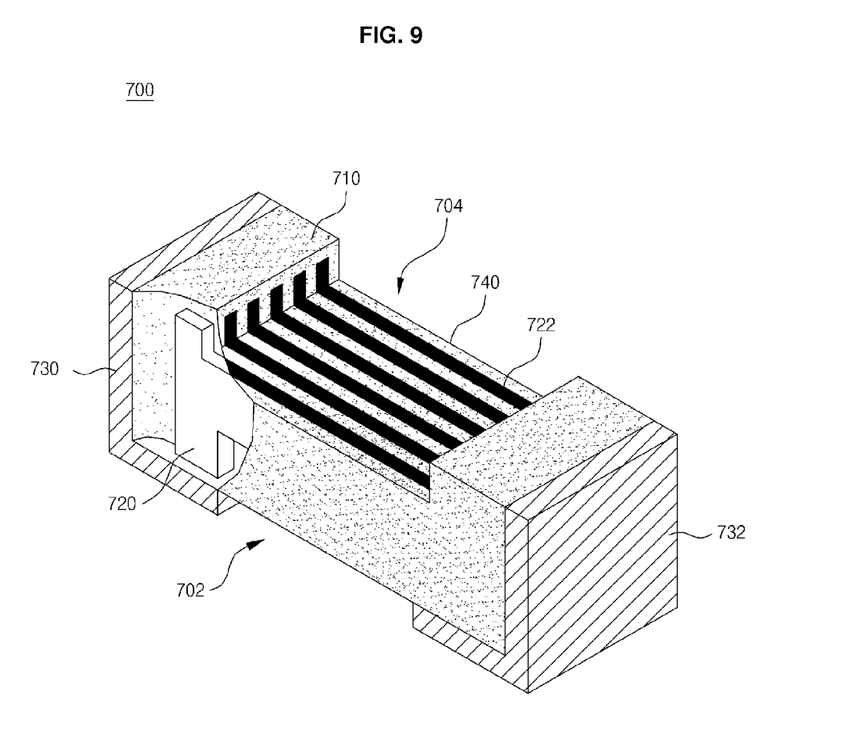
FIG. 9 is a perspective view of a sensor according to further another embodiment of the present invention.

FIG. 9 is a view of a sensor 700 according to another embodiment of the present invention.

According to this embodiment, each of electrode terminals 730 and 732 disposed on side surfaces opposite to each other extends to a bottom surface of a sensing stack 702. An end of each of conductive layers 720 and 722 may has a pattern shape that is bent to the bottom surface of the sensing stack 702 and thus is electrically connected to each of the electrode terminals 730 and 732.

According to the above-described structure, the sensors may be easily mounted on a circuit board by using the electrode terminals 730 and 732 disposed on the bottom surface of the sensing stack 702.

Also, a sensing material may be filled into only a groove or slot 740 to cover the conductive layers 720 and 722 that are exposed through a bottom and sidewall of the groove or slot 740. Thus, the sensing material may be uniformly applied.

As seen from the above-described embodiments, the present invention has several advantages.

First, the sensor according to the present invention may be variously applied as a sensor for sensing bio-gas or infrared optical materials.

Also, the separation layer disposed between the conductive layers may be adjusted in thickness to provide a fine distance between the sensing electrodes. In addition, the sensing electrode for sensing may be easily adjusted in width or length, and the manufacturing process may be simplified to reduce the manufacturing costs.

Also, since the sensing electrode is embedded within the sensing stack, the short-circuit or disconnection of the electrode may not occur to improve reliability and sensitivity of the sensor.

Also, since the number of conductive layers is freely adjustable, the sensitivity may be adjusted. In addition, the sensor according to the present invention may function as one sensor or plurality of sensors without an existing multiplex type sensor in which a plurality of sensor are connected to each other in parallel or series to increase sensitivity.

It is to be understood that the above-described embodiments are merely illustrative of the present invention and that many variations of the above-described embodiments can be devised by those skilled in the art without departing from the scope of the invention.

What is claimed is:

1. A sensor having an embedded electrode, the sensor comprising:
   a sensing stack in which first and second conductive layers are stacked and embedded within a material, the material including a separation layer between the conductive layers; and
   a first and a second electrode terminals electrically connected to the first and second conductive layers, respectively, the electrode terminals being disposed on two opposing side surfaces of the sensing stack,
   wherein the first and second conductive layers are exposed to at least one side surface, except for the side surfaces on which the electrode terminals are disposed, to form a sensing surface,
   wherein at least one sensing material is applied on the sensing surface and forming a sensing material layer on the sensing surface for detecting target matter using the sensor.

2. The sensor of claim 1, wherein at least one slot is formed in the sensing surface over an overall region in the stacked direction, or at least one groove having a predetermined width is formed in the sensing surface.

3. The sensor of claim 1, wherein the side surface on which the electrode terminal is disposed and the sensing surface are vertically cut or polished to provide flat planes.

4. The sensor of claim 1, wherein the first and second conductive layers overlap each other, or embedded ends of the first and second conductive layers are spaced apart from each other and do not overlap each other.

5. The sensor of claim 1, wherein each of the first and second conductive layers consists of a long member and a short member with different lengths, the long and short members alternately arranged and spaced apart from each other.

6. The sensor of claim 1, wherein the electrode terminal is electrically separated and divided into a plurality of sub electrode terminals for each conductive layer to constitute a plurality of independent sensor modules.

7. The sensor of claim 6, wherein different numbers of the conductive layers are electrically connected to each of the plurality of sub electrode terminals, respectively.

8. The sensor of claim 1, wherein the electrode terminal extends to an opposite side surface of the sensing surface, and each of the first and second conductive layers is electrically connected to the electrode terminal at the extending portion of the electrode terminal.

9. The sensor of claim 1, wherein the separation layer is formed of insulating materials.

10. The sensor of claim 9, wherein the separation layer is formed of ceramic or resin.

11. The sensor of claim 1, wherein the at least one sensing material applied on the sensing surface contains platinum, and the sensor is for detecting presence of hydrogen or hydrogen compounds.

12. The sensor of claim 11, wherein a zinc oxide layer is deposited before applying the at least one sensing material containing platinum.

* * * * *